United States Patent [19]
Colby et al.

[11] Patent Number: 4,587,060

[45] Date of Patent: May 6, 1986

[54] STABILIZATION OF CYANOHYDRINS

[75] Inventors: Thomas H. Colby; Walter Dong, both of Houston, Tex.

[73] Assignee: Shell Oil Company, Houston, Tex.

[21] Appl. No.: 742,501

[22] Filed: Jun. 7, 1985

[51] Int. Cl.[4] ............................................ C07C 121/75
[52] U.S. Cl. .................................... 558/304; 558/410
[58] Field of Search ..................................... 260/465 F

[56] References Cited

U.S. PATENT DOCUMENTS 4,299,843 11/1981 Tieman et al. ...................... 424/305

FOREIGN PATENT DOCUMENTS 58-92648 6/1983 Japan.

OTHER PUBLICATIONS

"Preparative Organic Chemistry", pp. 875–877, Weygand and Helgetag (1972).

*Primary Examiner*—Dolph H. Torrence

[57] ABSTRACT

Cyanohydrins or a solution thereof in an inert solvent are stabilized by treatment with organophosphoric acids.

18 Claims, No Drawings

STABILIZATION OF CYANOHYDRINS

BACKGROUND OF THE INVENTION

1. Field of the Invention

The present invention relates to a process for stabilization of cyanohydrins.

2. Description of the Prior Art

It is known that strong acids such as sulfuric acid and phosphoric acid are used to stabilize cyanohydrins. It is also known from Japanese patent application 58/92,648 to use optionally substituted aromatic sulfonic acids to stabilize alpha cyano-3-phenoxy-benzyl alcohol against reversion to the corresponding aldehyde. However, the use of strong acids, including the above, have been found unsatisfactory to stabilize (optically-active) cyanohydrins for several reasons, including (a) degradation of residual aldehyde present in cyanohydrins, (b) absorption of moisture from wet products to form an aqueous phase in which the acid concentrates, and (c) low solubility in any organic phase containing the cyanohydrins. The present invention provides an improved process for the stabilization of cyanohydrins or a solution thereof in an inert solvent.

SUMMARY OF THE INVENTION

The present invention is directed to a method of stabilizing a cyanohydrin or a solution thereof in an inert solvent comprising treating the cyanohydrin or solution thereof with a stabilizing amount of an organophosphoric acid.

The cyanohydrins are stabilized against degradation, reversion to the aldehyde and/or racemization at the chiral carbon atom bearing the cyano group. The process is useful for stabilizing (chiral) cyanohydrins, known in the art as intermediates to biologically active materials, such as pyrethroid esters and the like, including aliphatic, cycloaliphatic and aryl cyanohydrins containing up to about 24 carbon atoms. In one embodiment, the cyanohydrin has the formula I

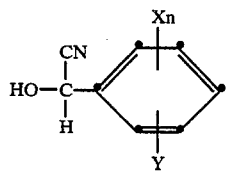

wherein X is a halogen atom having an atomic number of 9 to 35, inclusive, or a methyl group, n is 0, 1 or 2 and Y is a phenyl, phenoxy, benzyl, or phenylthio group each optionally substituted by one or two groups selected halogen atoms having an atomic number of 9 to 35, inclusive, or methyl groups. Preferably, Y is a 3-phenoxy group, n is 0 or 1 and when n is 1 then X is a 4-fluoro group.

A solution of the cyanohydrin in any inert solvent can also be stabilized according to the present invention. Suitable inert organic solvents include: lower alkane or aromatic hydrocarbons (e.g., hexane, heptane, benzene, toluene, xylene, etc.), halogenated alkane or aromatic hydrocarbons (e.g., chloroforn, carbon tetrachloride, dichloroethane, chlorobenzene, etc.)

The organophosphoric acids used in the present invention are generally known in the art. They should be relatively soluble in the organic phase (cyanohydrin and the optionally inert solvent) and insoluble in water. Since the organophosphoric acid compound must be substantially water-immiscible, the total number of carbon atoms in the molecule should be sufficient to render the compound substantially insoluble. For example, the organophosphoric acid compounds which can be utilized include acid compounds of the following formula II:

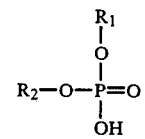

where $R_1$ and $R_2$ are selected from the group consisting of hydrogen alkyl, aryl, and aralkyl radicals, with the proviso that the sum of carbon atoms in $R_1$ and $R_2$ is generally at least 4 to 20 carbon atoms. $R_1$ and $R_2$ can usually be the same or different radical. The $R_1$ and $R_2$ groups can, of course, be substituted with a variety of groups such as alkoxy, halogen, etc., and $R_1$ and $R_2$ can be saturated or unsaturated or interrupted by hetero atoms so long as there is no interference in the performance of the compound in stabilizing the cyanohydrin. In one embodiment, the organophosphoric acid has the formula II above wherein $R^1$ is a hydrogen atom, an alkyl, aryl or aralkyl group containing up to 20 carbon atoms each optionally substituted by one or more halogen atoms or alkoxy groups containing 1 to 4 carbon atoms in the alkyl portion and $R^2$ is alkyl, aryl or aralkyl group containing up to 20 carbon atoms, each optionally substituted by one or more halogen atoms or alkoxy gropus containing 1 to 4 carbon atoms in the alkyl portion.

Organophosphoric acid compounds which can be advantageously used according to this invention include 2-ethylhexyl dihydrogen phosphate, di(2-ethylhexyl) hydrogen phosphate, heptadecyl dihydrogen phosphate, dodecyl dihydrogen phosphate, di(1-methyl-heptyl) hydrogen phosphate, diisooctyl hydrogen phosphate, di(2-ethyl-4-methyl-pentyl) hydrogen phosphate, di(2-propyl-4-methyl-pentyl) hydrogen phosphate, octylphenyl dihydrogen phosphate, the isooctyl or stearyl derivatives of alkyl acid phosphates and the like.

In one embodiment, the organophosphoric acid is an alkyl or dialkylphosphoric acid in which $R_1$ is a hydrogen atom or an alkyl group containing from 1 to 10 carbon atoms and $R_2$ is an alkyl group, containing from 4 to 10 carbon atoms. For example, the acid is 2-ethylhexyl dihydrogen phosphate, di-(2-ethylhexyl) hydrogen phosphate or mixtures thereof.

These non-volatile organophosphoric acids are used to stabilize chiral cyanohydrins under various temperature conditions and are particularly useful below about 100° C., preferably below about 75° C. Essentially complete stabilization is obtained at ambient temperatures of about 25° C. and the like. In one embodiment, the acids are used to stabilize chiral cyanohydrins during recovery and are therefore particularly useful at temperatures between about 60°–100° C. and, preferably between about 60°–75° C., particularly where the residence time at such temperatures is less than about one and one-half hours, or, preferably, less than about one-half hours, as during flashing wet chiral cyanohydrin to recover solvent and remove excess HCN.

The amount of the organophosphoric acid used is sufficient to stabilize the (chiral) cyanohydrin against degradation, reversion to the aldehyde and/or racemization. In one embodiment of the invention, the organophosphoric acid is used in an amount of from about 0.01 to about 0.20% weight based upon the cyanohydrin. Preferably, the organophosphoric acid is used in an amount of from about 0.02 to about 0.10% weight based upon the cyanohydrin.

DESCRIPTION OF THE PREFERRED EMBODIMENT

A preferred embodiment of the present invention is directed to stabilizing a cyanohydrin or a solution thereof in an inert aliphatic or aromatic hydrocarbon solvent is treated with an organophosphoric acid containing 4 to 20 carbon atoms. Preferably the cyanohydrin is a pyrethroid alpha-cyano-3-phenoxy benzyl alcohol and has the formula

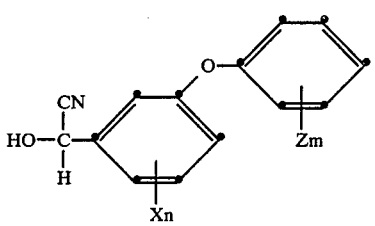

wherein X and Z each independently is a halogen atom having an atomic number of from 9 to 35, inclusive and m and n each independently is 0 or 1. Preferably, m is 0 and n is 0 or 1 and when n is 1 then x is a 4-fluoro group. These cyanohydrins are well known intermediates to pyrethroid esters. The stabilization of such cyanohydrins, particularly when they are substantially in the (S)-absolute isomer configuration or a mixture enriched therein is highly desirable. Moreover, it is desirable to stablize this (S)-form unitl esterification to an ester having substantially the S-configuration in the alchohol moiety or enriched in the S-configuration. Yet, the stabilizer must be readily removable by methods of ester purification conventionally used. In the case of stripping, the present organophosphoric acid stabilizer is preferred, which is essentially non-volatile as compared to the pyrethroid ester.

ILLUSTRATIVE EMBODIMENTS

The present invention is illustrated by the following Embodiments, which should not be regarded as limiting the invention in any way.

EMBODIMENTS 1-6

Solutions of S-alpha-cyano-3-phenoxybenzyl alcohol in toluene were prepared, treated with an organophosphoric acid. Subsamples were prepared and held at a constant ambient temperature of 23°-25° C. for various periods of time at which the percentage of S-chiral isomer content was determined. Results of these tests are set forth in Table 1 below.

TABLE 1

STABILIZATION OF S—ALPHA-CYANO-3-PHENOXYBENZYL ALCOHOL WITH ORGANOPHOSPHORIC ACIDS

| Embodiment | Stabilizer | Concentration % | Alcohol Concentration % | Time Days | S—isomer content % |
|---|---|---|---|---|---|
| 1 | none | | 55 | 0 | 95.2 |
| | | | | 215 | 69.5 |
| 2 | DEHPA[b] | 0.17 | 55 | 0 | 94.6 |
| | | | | 104 | 94.1 |
| | | | | 166 | 92.1 |
| | | | | 234 | 94.5 |
| 3 | 50% EHPA[c] 50% DEPHA | 0.10 | 69 | 0 | 91.5 |
| | | | | 73 | 90.9 |
| | | | | 135 | 90.6 |
| | | | | 218 | 91.1[a] |
| 4 | 50 EHPA 50% DEPHA | 0.06 | 64 | 0 | 92.5 |
| | | | | 50 | 92.3 |
| | | | | 113 | 92.6 |
| 5 | 50% EHPA 50% DEPHA | 0.055 | 66 | 0 | 93.6 |
| | | | | 49 | 92.9 |
| | | | | 112 | 93.6 |
| | | | | 172 | 94.3[a] |
| 6 | 50% EHPA 50% DEPHA | 0.03 | 69 | 0 | 94.8 |
| | | | | 51 | 94.8 |
| | | | | 114 | 94.8 |
| | | | | 172 | 94.9[a] |

[a] These samples periodically reached 30° C. in last 90 days.
[b] DEHPA means di-(2-ethylhexyl) hydrogen phosphate.
[c] EHPA means 2-ethylhexyl dihydrogen phosphate.

EMBODIMENTS 7-11

Solutions of S-alpha-cyano-3-phenoxybenzyl alcohol in toluene were prepared, treated with an organophosphoric acid. Subsamples were prepared and held at a constant temperature of 50°-55° C. for various periods of time at which the percentage of S-chiral isomer content was determined. Results of these tests are set forth in Table 2 below.

TABLE 2

STABILIZATION OF S—ALPHA-CYANO-3-PHENOXYBENZYL ALCOHOL WITH ORGANOPHOSPHORIC ACIDS

| Embodiment | Stabilizer | Concentration % | Time Days | S—isomer content % |
|---|---|---|---|---|
| 7 | DEHPA[a] | 0.13 | 0 | 93.3 |
| | | | 7 | 91.6 |
| | | | 18 | 91.5 |
| | | | 26 | 91.6 |
| | | | 43 | 91.8 |
| | | | 82 | 89.7 |
| 8 | EHPA[b] | 0.03 | 0 | 94.9 |
| | | | 7 | 94.4 |
| | | | 18 | 93.7 |
| | | | 26 | 93.3 |
| | | | 43 | 91.9 |
| | | | 82 | 87.5 |
| | | | 91 | 86.5 |
| 9 | EHPA | 0.055 | 0 | 94.3 |
| | | | 7 | 94.0 |
| | | | 18 | 93.9 |
| | | | 26 | 94.0 |
| | | | 43 | 94.5 |
| | | | 82 | 93.1 |
| 10 | EHPA | 0.1 | 0 | 91.1 |
| | | | 7 | 90.9 |
| | | | 18 | 90.5 |
| | | | 26 | 91.2 |
| | | | 35 | 91.6 |
| | | | 43 | 92.2 |
| | | | 82 | 90.6 |
| 11 | EHPA | 0.15 | 0 | 94.9 |
| | | | 0 | 95.4 |
| | | | 15 | 95.5 |
| | | | 23 | 94.5 |
| | | | 49 | 95.1 |

TABLE 2-continued

STABILIZATION OF S—ALPHA-CYANO-
3-PHENOXYBENZYL ALCOHOL WITH
ORGANOPHOSPHORIC ACIDS

| Embodiment | Stabilizer | Concentration % | Time Days | S—isomer content % |
|---|---|---|---|---|
| | | | 71 | 96.0 |
| | | | 86 | 95.9 |

[a] DEHPA means di-(2-ethylhexyl) hydrogen phosphate.
[b] EHPA means 2-ethylhexyl dihydrogen phosphate.

EMBODIMENTS 12-13

Solutions of S-alpha-cyano-3-phenoxybenzyl alcohol in toluene were prepared, treated with an organophosphoric acid. These samples were treated in a toluene flasher for various periods of time and at various temperatures, after which the percentage of S-chiral isomer content of the recovered alpha-cyano-3-phenoxybenzyl alcohol was determined. Results of these tests are set forth in Table 3 below.

TABLE 3

STABILIZATION OF S—ALPHA-CYANO-3-PHENOXYBENZYL
ALCOHOL IN A TOLUENE FLASHER

| Embodiment | Stabilizer | Conc., % w | Feed Analysis[c] POAL % w | Feed Analysis[c] Alpha % | Flasher Cond. Temp. °C. | Flasher Cond. Residence Time Min. | Product Anal.[c] POAL % w | Product Anal.[c] Alpha % |
|---|---|---|---|---|---|---|---|---|
| 12 | DEHPA[a] | 0.13 | 5.2 | 92.2 | 75 | 88 | 4.3 | 93 |
| | | 0.11 | 3.8 | 94.5 | 85 | 66 | 4.7 | 93 |
| | | 0.13 | 5.2 | 92.2 | 100 | 45 | 9.6 | 93.3 |
| | | 0.24 | 3.8 | 95.7 | 100 | 55 | 8.9 | 94.2 |
| 13 | EHPA[b] | 0.05 | 4.6 | 91.7 | 76 | 8 | 4.4 | 90.3 |
| | | 0.1 | 4.9 | 94.9 | 75-80 | 15 | 3.5 | 94.5 |
| | | .02-.06 | 4.1[d] | 93.6[d] | 100 | 15-25 | 4.7[d] | 93.2[d] |
| | | 0.1 | 4.9 | 92.5 | 95-100 | 10-12 | 4.9 | 91.5 |

[a] DEHPA means di-(2-ethylhexyl) hydrogen phosphate.
[b] EHPA means 2-ethylhexyl dihydrogen phosphate.
[c] Solvent-free basis
[d] Average values

What is claimed is:

1. A method of stabilizing a cyanohydrin or a solution thereof in an inert solvent comprising treating the cyanohydrin or solution thereof with a stabilizing amount of a substantially water-immiscible organophosphoric acid.

2. A method according to claim 1 wherein the cyanohydrin has the formula I

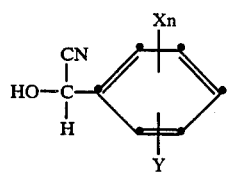

wherein X is a halogen atom having an atomic number of 9 to 35, inclusive, or a methyl group, n is 0, 1 or 2 and Y is a phenyl, phenoxy, benzyl or phenylthio group each optionally substituted by one or two groups selected halogen atoms having an atomic number of 9 to 35, inclusive, or methyl groups.

3. A method according to claim 2 wherein Y is a 3-phenoxy group.

4. A method according to claim 3 wherein n is 0 or 1 and when n is 1 then X is a 4-fluoro group.

5. A method according to claim 1 wherein the organophosphoric acid contains 4 to 20 carbon atoms.

6. A process according to claim 5 wherein the organophosphoric acid has the formula II

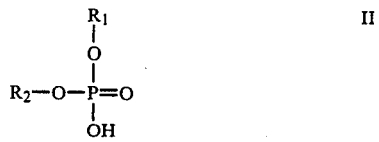

wherein $R^1$ is a hydrogen atom, an alkyl, aryl or aralkyl group containing up to 20 carbon atoms each optionally substituted by one or more halogen atoms or alkoxy groups containing 1 to 4 carbon atoms in the alkyl portion and $R^2$ is alkyl, aryl or aralkyl group containing up to 20 carbon atoms, each optionally substituted by one or more halogen atoms or alkoxy gropus containing 1 to 4 carbon atoms in the alkyl portion.

7. A method according to claim 5 wherein the organophosphoric acid is an alkyl or dialkyl phosphoric acid wherein $R_1$ is a hydrogen atom or an alkyl group containing from 1 to 10 carbon atoms and $R_2$ is an alkyl group containing from 4 to 10 carbon atoms.

8. A method according to claim 7 wherein the acid is 2-ethylhexyl dihydrogen phosphate, di-(2-ethylhexyl) hydrogen phosphate or mixtures thereof.

9. A method according to claim 1 wherein the organophosphoric acid is used in an amount of from about 0.01 to about 0.20% weight based upon the cyanohydrin.

10. A method according to claim 9 wherein the organophosphoric acid is used in an amount of from about 0.02 to about 0.10% weight based upon the cyanohydrin.

11. A method according to claim 1 wherein the solvent is an aliphatic or aromatic hydrocarbon.

12. A method according to claim 11 wherein the solvent is heptane or toluene.

13. A method according to claim 12 wherein the solvent is toluene.

14. A method according to claim 1 wherein a cyanohydrin or a solution thereof in an aliphatic or aromatic hydrocarbon solvent is treated with an organophosphoric acid containing up to 20 carbon atoms.

15. A method according to claim 14 wherein the cyanohydrin is chiral and has the formula

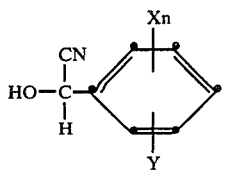

wherein X is a halogen atom having an atomic number of 9 to 35, inclusive, or a methyl group, n is 0, 1 or 2 and Y is a phenyl, phenoxy, benzyl or phenylthio group each optionally substituted by one or two groups selected halogen atoms having an atomic number of 9 to 35, inclusive, or methyl groups.

16. A method according to claim 15 wherein Y is a 3-phenoxy group.

17. A method according to claim 16 wherein n is 0 or 1 and when n is 1 then X is a 4-fluoro group.

18. A method according to claim 17 wherein (S)-alpha-3-phenoxybenzyl alcohol or a solution thereos in a solvent is stabilized with 2-ethylhexyl dihydrogen phosphate, di-(ethylhexyl) hydrogen phosphate or mixtures of such acids.

* * * * *